US00PP36839P3

(12) United States Plant Patent
Volz

(10) Patent No.: US PP36,839 P3
(45) Date of Patent: Jul. 22, 2025

(54) APPLE TREE NAMED 'PremA047'

(50) Latin Name: *Malus domestica*
Varietal Denomination: PremA047

(71) Applicant: Prevar Limited, Hastings (NZ)

(72) Inventor: Richard Volz, Auckland (NZ)

(73) Assignee: Prevar Limited, Hastings (NZ)

( * ) Notice: Subject to any disclaimer, the term of this patent is extended or adjusted under 35 U.S.C. 154(b) by 0 days.

(21) Appl. No.: 18/909,307

(22) Filed: Oct. 8, 2024

(65) Prior Publication Data

US 2025/0120328 P1 Apr. 10, 2025

Related U.S. Application Data

(60) Provisional application No. 63/589,163, filed on Oct. 10, 2023.

(51) Int. Cl.
*A01H 5/08* (2018.01)
*A01H 6/74* (2018.01)

(52) U.S. Cl.
USPC ..... Plt./161
CPC ..... *A01H 6/7418* (2018.05)

(58) Field of Classification Search
USPC ..... Plt./161
CPC ..... A01H 5/08; A01H 5/00; A01H 6/7418; A01H 6/74
See application file for complete search history.

(56) References Cited

U.S. PATENT DOCUMENTS

PP33,545 P2 * 10/2021 Volz ..... Plt./161

* cited by examiner

*Primary Examiner* — June Hwu
(74) *Attorney, Agent, or Firm* — Michelle Bos Legal LLC

(57) ABSTRACT

A new and distinct apple tree named 'PremA047', the fruit of which is notable for its intense red skin color, low susceptibility to russet, and excellent storage characteristics.

7 Drawing Sheets

Latin name: *Malus domestica.*
Variety denomination: 'PremA047'.

BACKGROUND AND SUMMARY OF THE INVENTION

The new apple tree 'PremA047' was created in the course of a planned breeding program carried out at Havelock North, New Zealand. 'PremA047' originated as a result of a controlled cross made in 2009 of female parent 'Scifresh' (U.S. Plant Pat. No. 13,888) and male parent 'A174R01T204' (not patented). 'PremA047' was selected as a single plant from among a population of seedlings derived from the parents, and was initially observed for its attractive fruit with intense red skin color and low susceptibility to russet, its harvest timing, and for its excellent storage characteristics. The plant was first asexually propagated by grafting in 2014 at Havelock North, New Zealand, and has since been observed to retain its desirable characteristics and reproduce true to type over a number of asexually propagated generations.

'PremA047' is distinguished from parent varieties 'Scifresh' and 'A174R01T204', and from similar variety 'Galaxy' (U.S. Plant Pat. No. 6,955) as set forth in Tables 1, 2 and 3.

TABLE 1

Comparison of 'PremA047' to 'Scifresh'

| Characteristic | 'PremA047' | 'Scifresh' |
|---|---|---|
| Fruit - skin background color | Yellow 4B to 4C | Yellow 8A |

TABLE 1-continued

Comparison of 'PremA047' to 'Scifresh'

| Characteristic | 'PremA047' | 'Scifresh' |
|---|---|---|
| Fruit - skin overcolor | Solid flush greyed purple 187A to 187B over 90% to 100% of skin surface | Red 42C with narrow stripes of greyed-red 179A over about 75% of skin surface |

TABLE 2

Comparison of 'PremA047' to 'A174R01T204'

| Characteristic | 'PremA047' | 'A174R01T204' |
|---|---|---|
| Fruit - skin overcolor | Solid flush greyed purple 187A to 187B over 90% to 100% of skin surface | Solid flush burnt red |
| Fruit shape | Globose conical | Conical |
| Bark texture | Moderately rough | Rough, scaly |
| Harvest maturity | Later | Earlier, similar to 'Scifresh' |

TABLE 3

Comparison of 'PremA047' to 'Galaxy'

| Characteristic | 'PremA047' | 'Galaxy' |
|---|---|---|
| First bloom | Mid-September (Havelock North, NZ) | 2 to 3 weeks after 'PremA047' |
| Pattern of overcolor | Solid flush | Striped |

BRIEF DESCRIPTION OF THE PHOTOGRAPHS

The attached photographs showing 'PremA047' apple trees and fruit were taken during the 2023-2024 growing season at Havelock North, New Zealand. The trees depicted are 9 years old, having been grown in the nursery for 2 years and field-planted in 2016.

BOTANICAL DESCRIPTION OF THE VARIETY

Figure 1:
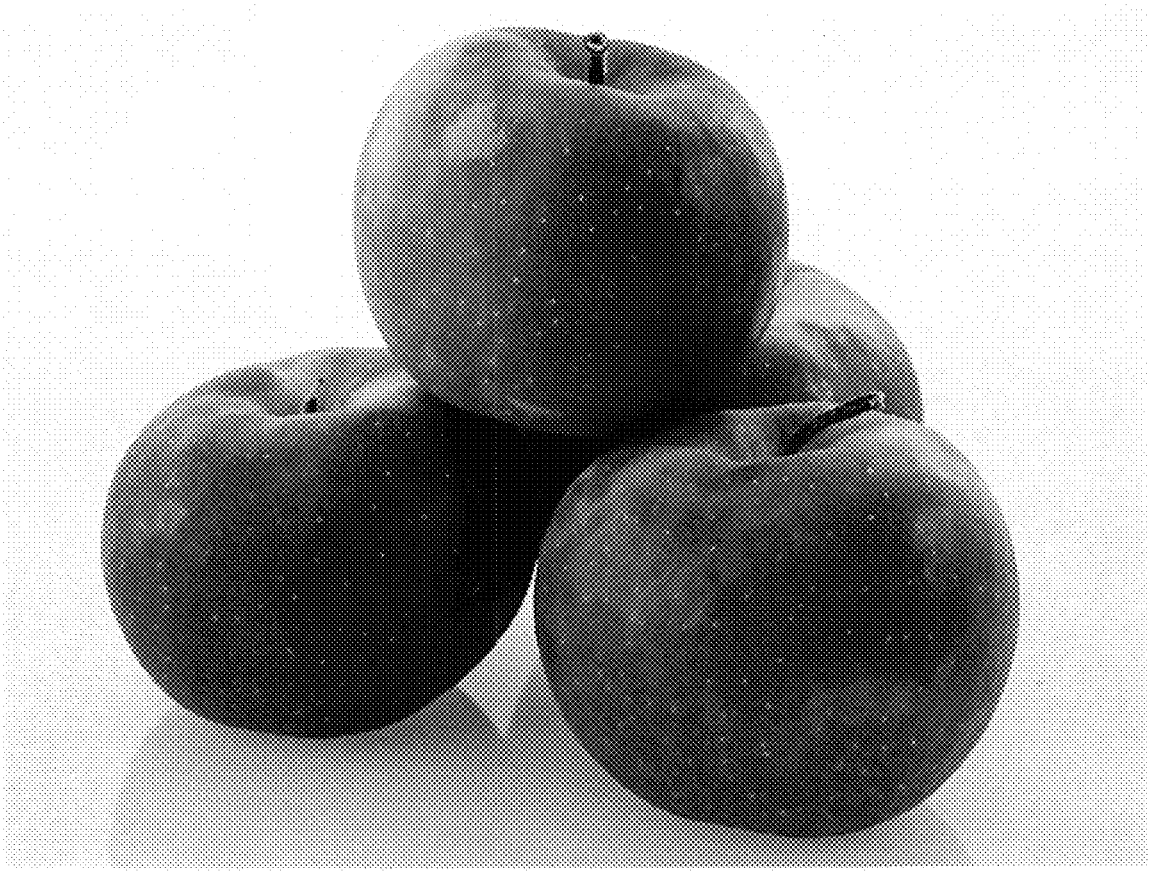
FIG. 1 shows fruit of 'PremA047'.
Figure 2:
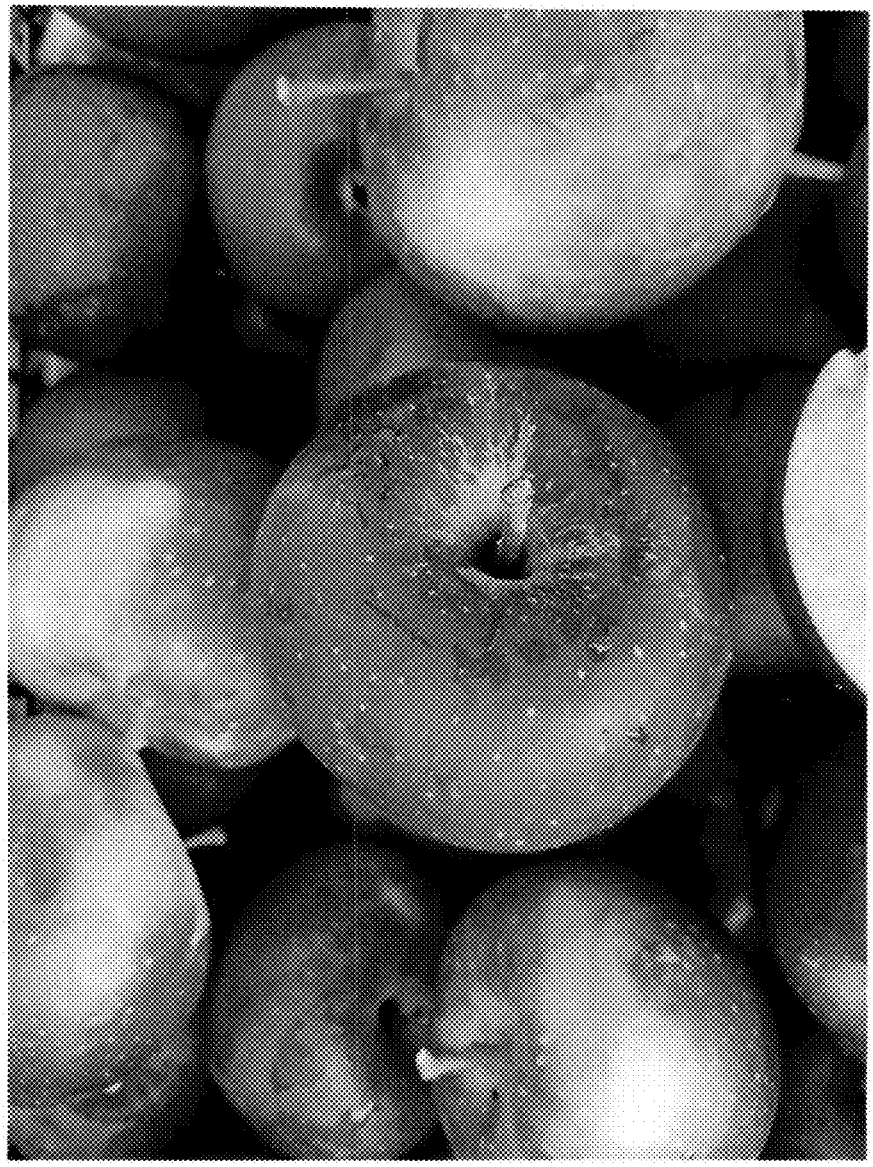
FIG. 2 shows fruit of 'PremA047'.
Figure 3:
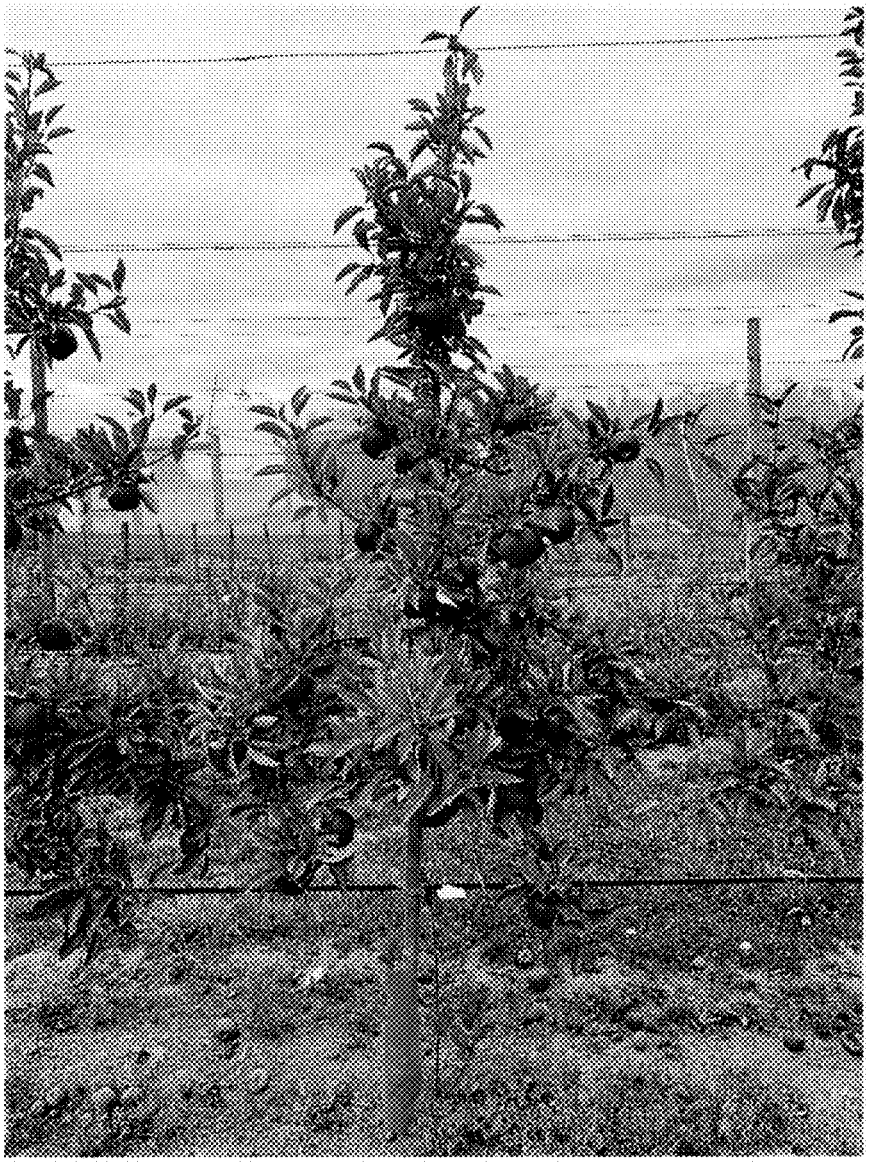
FIG. 3 shows a tree, fruit and leaves of 'PremA047'.
Figure 4:
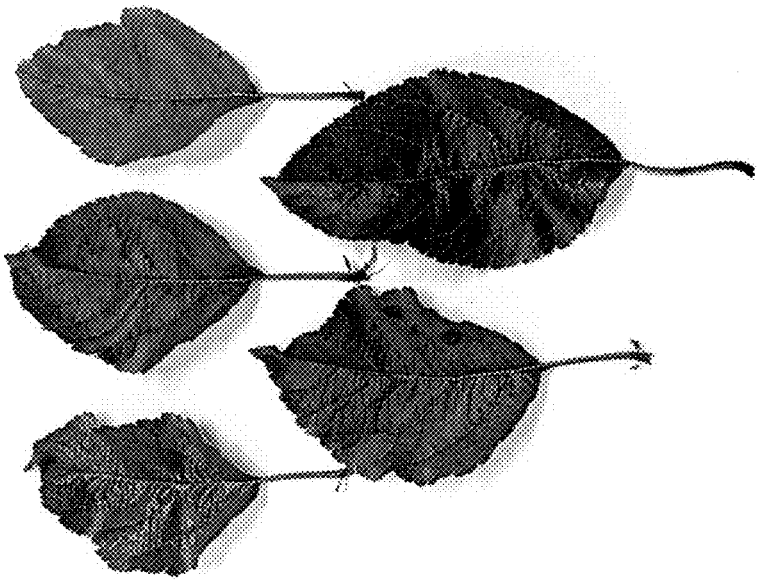
FIG. 4 shows the upper surface of leaves of 'PremA047'.
Figure 5:
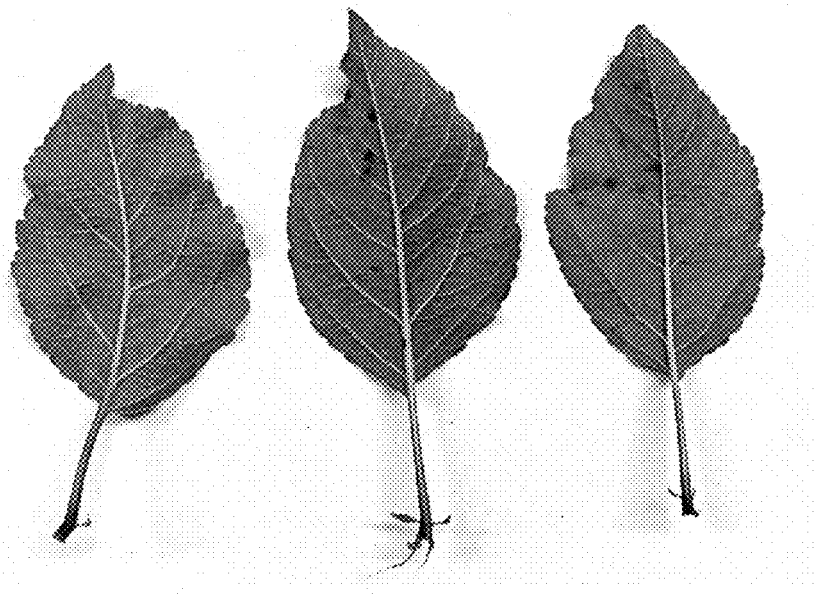
FIG. 5 shows the lower surface of leaves of 'PremA047'.
Figure 6:
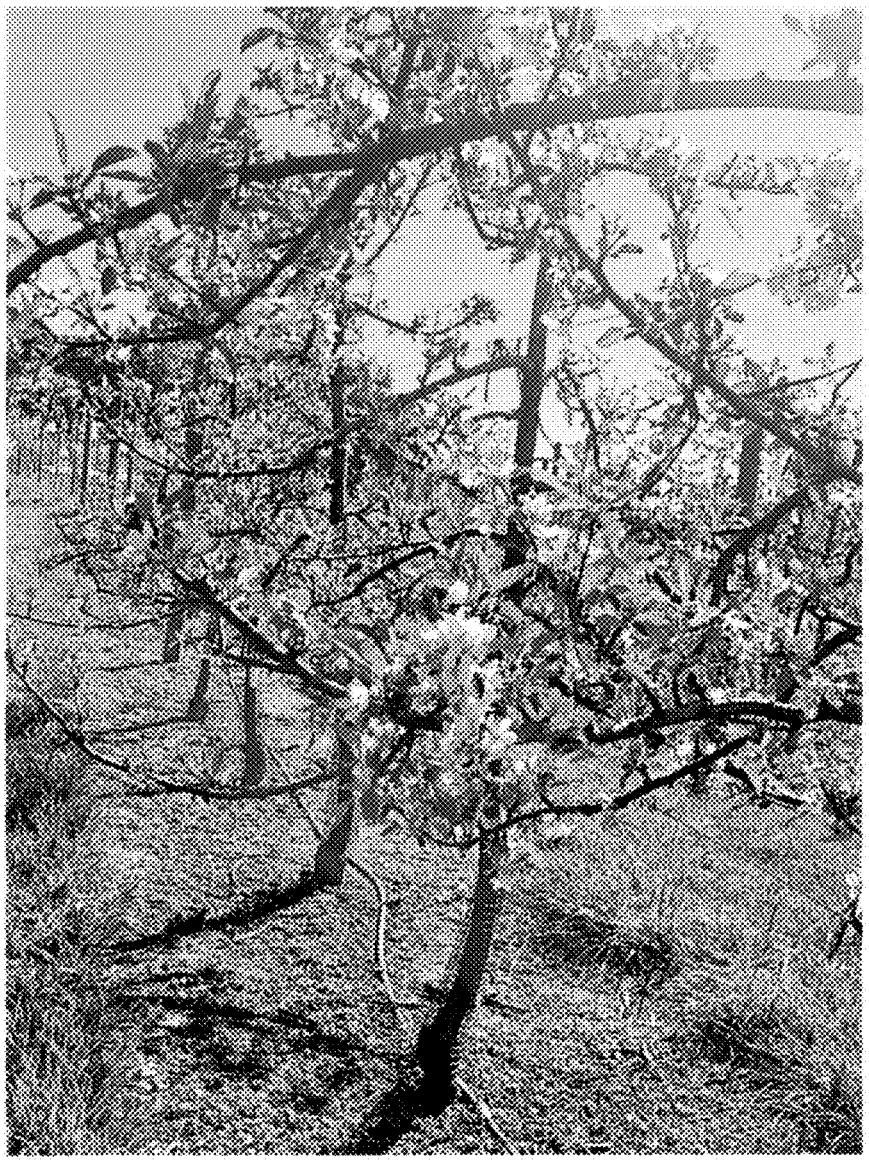
FIG. 6 shows a tree, blossoms and young leaves of 'PremA047'.
Figure 7:
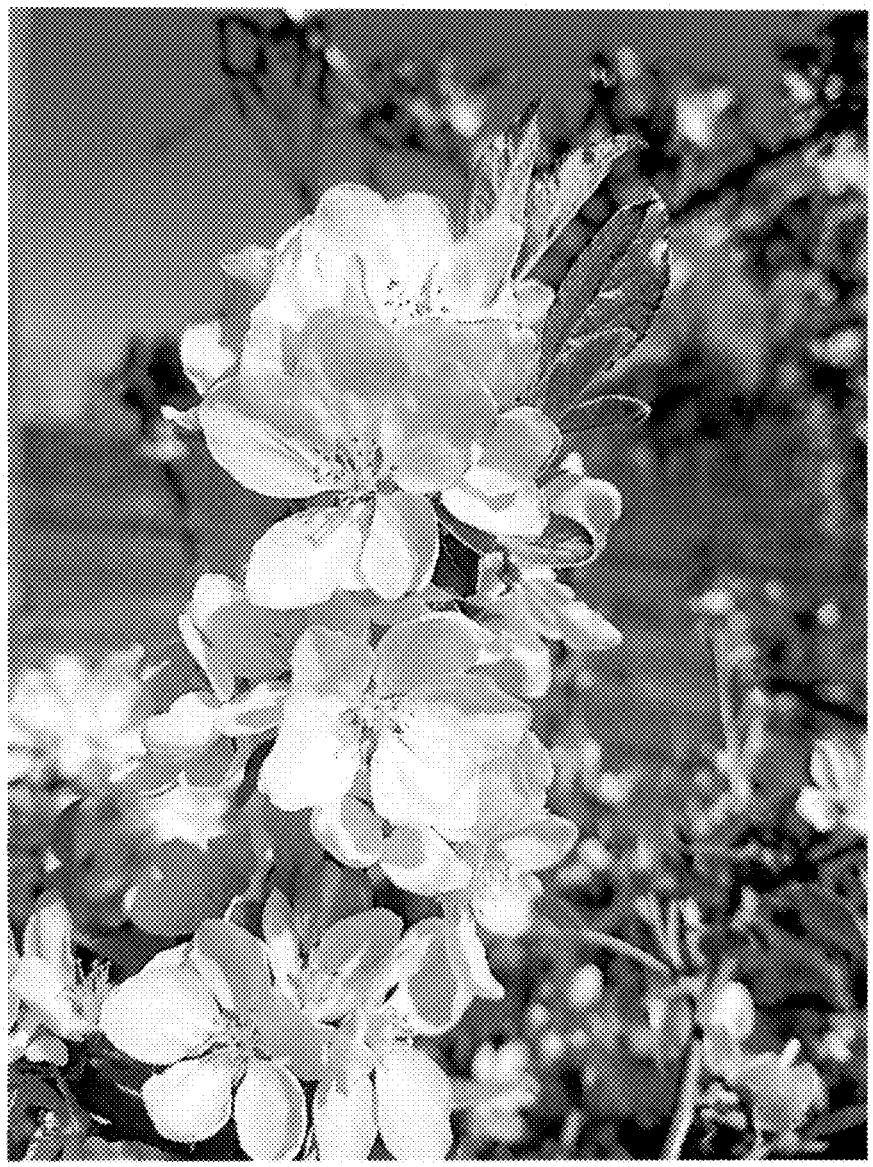
FIG. 7 shows blossoms of 'PremA047'.
Figure 8:
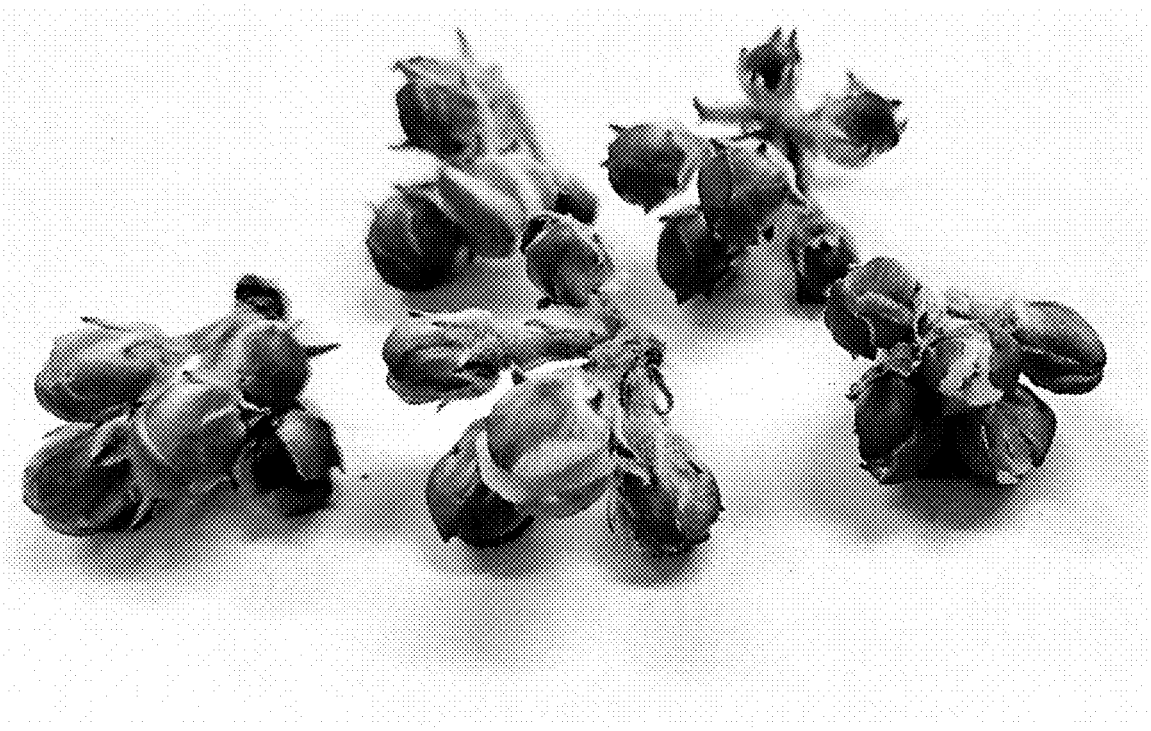
FIG. 8 shows flower buds of 'PremA047'.

The following detailed botanical description is based on observations of 'PremA047' trees on 'M9' rootstock (not patented) planted at Havelock North, New Zealand. The trees were 9 years old when described during the 2023-2024 season, having been grown in the nursery for 2-years before field-planting in 2016. It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average. Color descriptions are made with reference to The R.H.S. Colour Chart, $6^{th}$ ed. (Royal Horticultural Society, London, 2015).

Tree: Trees of 'PremA047' are somewhat vigorous, have an upright to spreading growth habit, and tend to be shorter and more compact than 'Galaxy' Gala (U.S. Plant Pat. No. 6,955) and 'CABp Fuji' (U.S. Plant Pat. No. 17,914), while the trunk of 'PremA047' has a cross-sectional area similar to both varieties, as detailed in Table 4.

TABLE 4

Comparison of height and trunk cross-sectional area at third leaf

| | Tree Height | Trunk Cross-Sectional Area |
|---|---|---|
| PremA047 | 2.6 m | 10 $cm^2$ |
| Galaxy Gala | 3.3 m | 10.1 $cm^2$ |
| CABp Fuji | 3.0 m | 10 $cm^2$ |

*Vigor.*—Medium.
*Type.*—Ramified.
*Habit.*—Upright to spreading.
*Spread of mature tree.*—2.1 m.
*Height.*—3.4 m.
*Trunk diameter at 30 cm above graft.*—19.9 cm.
*Bearing.*—On spurs.
*Bark texture.*—Moderately rough.
*Bark color.*—Grey-brown 197C.
*Lenticel length.*—6 mm.
*Lenticel width.*—2 mm to 3 mm.
*Lenticel shape.*—Elongated.
*Lenticel color.*—Grey-brown N199A.
*Lenticel density.*—16 to 22 per 10 $cm^2$.

Fruiting branches:
*Length.*—77.2 cm.
*Diameter.*—13.5 mm.
*Crotch angle.*—80° to 95° (trained).
*Bark color.*—Grey-brown N199C.
*Lenticel length.*—1.9 mm to 3.1 mm.
*Lenticel width.*—1 mm to 1.2 mm.
*Lenticel shape.*—Elongated and vertically oriented.
*Lenticel color.*—Yellow-green 153B.
*Lenticel density.*—5 to 7 per $cm^2$.

One-year-old shoot:
*Length.*—29.2 cm.
*Diameter.*—7.7 mm.
*Internode length.*—3 cm.
*Pubescence.*—Present.
*Color.*—Grey-brown N199D.
*Lenticel length.*—1.5 mm to 2 mm.
*Lenticel width.*—0.5 mm to 1 mm.
*Lenticel shape.*—Round to elongated.
*Lenticel density.*—6 per $cm^2$.

Flowers: 'PremA047' blooms 2 to 3 weeks earlier than 'Galaxy', with a bloom period of 3 to 4 weeks. The presence of the S2 and S5 self-incompatibility alleles in 'PremA047' makes it pollen-compatible with nearly all major commercial cultivars grown in the area where tested.

Flower buds:
*State described.*—First pink.
*Quantity per spur.*—5.1 (mean).
*Bud shape.*—Round.
*Apex shape.*—Rounded.
*Length.*—9.4 mm.
*Diameter.*—8.2 mm.
*Color.*—Red-purple 64B at first pink; Purple 76D at balloon stage.

Blooms:
*Diameter of fully open flower.*—37 mm.
*Depth of fully open flower.*—12.5 mm.
*Relative position of petal margin.*—Not touching.
*Average number of flowers per cluster.*—4.4.
*First bloom.*—Sep. 21, 2023 (Havelock North, NZ).
*Full bloom.*—Oct. 7, 2023 (Havelock North, NZ).
*Pollinator.*—*Malus floribunda.*

Flower petals:
*Number per flower.*—5.
*Petal shape.*—Obovate.
*Length.*—18 mm.
*Width.*—11.6 mm.
*Apex shape.*—Rounded to obtuse.
*Base shape.*—Obtuse.
*Margin.*—Mildly undulating.
*Color.*—Upper surface — White N155B.
*Color.*—Lower surface — Purple 76D with streaks of purple 76B.

Pistils:
*Length.*—8.4 mm.
*Average quantity per flower.*—7.
*Color.*—Yellow-green 145C.
Stigma:
*Position relative to anthers.*—Same level.
*Diameter.*—0.5 mm to 1 mm.
*Color.*—Yellow-green 151C.
Style:
*Length.*—8.9 mm.
*Color.*—Yellow-green 151C.
Stamens:
*Average quantity per flower.*—15.
*Length.*—9 mm.
*Anther color.*—Yellow 3B.
*Pollen color.*—Yellow 4B.
*Pollen.*—Present, abundant.
Pedicel:
*Length.*—23 mm.
*Diameter.*—1.5 mm.
*Color.*—Yellow-green 144B with greyed-orange 177A.
Sepals:
*Quantity per flower.*—5.
*Color.*—Yellow-green 145A.
*Length.*—5 mm.
*Shape.*—Broad triangle.
*Apex shape.*—Acute.
*Margin.*—Smooth, reflexed.
Leaves:
*Shape.*—Ovate.
*Length.*—103 mm.
*Width.*—56 mm.
*Length to width ratio.*—1.84.
*Margin.*—Crenate.
*Apex shape.*—Acuminate.
*Base shape.*—Oblique.
*Color.*—Upper surface — Green N137B.
*Color.*—Lower surface — Yellow-green 144A.
*Attitude in relation to shoot.*—Upwards.
Petiole:
*Length.*—32.6 mm.
*Diameter.*—1.9 mm.
*Color.*—Yellow-green 145B; greyed-purple 184B anthocyanin present primarily at attachment end.
Fruit: The mean fruit weight for 'PremA047' fruits from 3$^{rd}$ leaf trees is 199 g, which is similar to fruits of 'CABp Fuji' and smaller than fruits of 'Galaxy' gala. The shape of fruits of 'PremA047' is globose-conical and symmetrical, with the broadest point at the fruit equator or above. Harvest yield for third leaf trees of 'PremA047' ranged from 14.5 to 20.3 metric tons per hectare, with an average of 18 MT/ha. Fruits of 'PremA047' have been observed to have a pleasing fruity flavor with low to moderate acid-sugar balance. When comparing the harvest characteristics of 'PremA047' fruit with those of 'Galaxy' Gala and 'CABp Fuji', 'PremA047' fruit was observed to be 0.7 to 0.8 kgf more firm than 'Galaxy' Gala and 1.2 to 1.4 kgf more firm than 'CABp Fuji'. 'PremA047' fruit had similar soluble solids and acidity contents to 'CABp Fuji' and had 1.8% to 2.0% higher soluble solids content as compared to 'Galaxy'.
*Quantity per cluster.*—2 to 3 after thinning.
*Height.*—65.7 mm.
*Diameter.*—83.6 mm.
*Ratio of height to width.*—0.79.
*Weight.*—235.7 g.
*General shape in profile.*—Globose conical.
*Position of maximum diameter.*—At or above equator.
*Ribbing.*—Moderate.
*Crowning at calyx end.*—Absent to weak.
*Size of eye.*—Medium.
*Aperture of eye.*—Closed.
*Depth of eye basin.*—33.12 mm.
*Width of eye basin.*—10.12 mm.
*Length of sepal.*—4 mm to 7 mm.
*Bloom of skin.*—Present in moderate amount.
*Greasiness of skin.*—Weak.
*Background color of skin.*—Yellow 4B to 4C.
*Over color of skin.*—Grey-purple 187A to 187B.
*Amount of over color.*—High to very high, 90% to 100%.
*Intensity of over color.*—Very dark.
*Pattern of over color.*—Solid flush.
*Amount of russet around stalk cavity.*—Absent to small.
*Amount of russet on cheeks.*—Minimal.
*Area of russet around eye basin.*—Small.
*Length of stalk.*—22.17 mm.
*Thickness of stalk.*—2.66 mm.
*Depth of stalk cavity.*—17.68 mm.
*Width of stalk cavity.*—38 64 mm.
*Stalk color.*—Greyed-orange 166B.
*Firmness of flesh.*—8.66 kgf.
*Flesh texture.*—Fine to medium.
*Aroma.*—Absent to very weak.
*Juiciness.*—Medium.
*Brix.*—15.7%.
*Flesh color.*—Yellow 8D, uniform throughout.
*Secondary flesh color.*—None.
*Number of lenticels.*—Few to medium.
*Size of lenticels.*—Less than 1 mm.
Seeds:
*Quantity per fruit.*—5 to 8.
*Shape.*—Ovate.
*Color.*—Brown 200B.
*Length.*—9.57 mm.
*Width.*—5.83 mm.
Harvest:
*Harvest date.*—Midseason; Apr. 2, 2024 (after 'Scifresh' and 'A174R01T204', similar to 'Scilate' U.S. Plant Pat. No. 20,477).
*Number of picks.*—One.
*Number of fruits produced per tree per harvest.*—60+.
Disease and pest susceptibility: 'PremA047' is susceptible to black spot (*Mycosphaerella pomi*), fire blight (*Erwinia amylovora*), and is sensitive to European canker (*Neonectria ditissima*).
Storageability: Stores well for 6 months with 1-MCP; exhibits a very low incidence of fruit storage disorders, with incidence less than 1% for soft scald and 1.5% for lenticel defect.
Market use: Fresh local market and export.
The invention claimed is:
1. A new and distinct apple tree named 'PremA047' substantially as described and illustrated herein.

* * * * *